US006271442B1

(12) United States Patent
Schell et al.

(10) Patent No.: US 6,271,442 B1
(45) Date of Patent: *Aug. 7, 2001

(54) METHOD OF PRODUCING PATHOGEN-RESISTANT PLANTS

(75) Inventors: Jeff Schell; Jürgen Logemann; Guido Jach, all of Köln (DE); John Mundy, Copenhagen (DK)

(73) Assignee: Max-Planck-Gesellschaft zur Forderung der Wissenschafen e.v. (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/775,362

(22) Filed: Jan. 3, 1997

Related U.S. Application Data

(63) Continuation of application No. 08/375,186, filed on Jan. 18, 1995, now Pat. No. 5,633,442, which is a continuation of application No. 07/810,390, filed on Dec. 19, 1991, now abandoned.

(30) Foreign Application Priority Data

Dec. 20, 1990 (DE) ................................. 40 40 954

(51) Int. Cl.[7] ........................... C12N 15/00; C12N 15/29; C12N 15/82; A01H 4/00
(52) U.S. Cl. ..................... 800/298; 800/295; 800/278; 435/69.1; 435/320.1; 435/419; 435/468; 435/252.3; 536/23.2; 536/23.6; 536/24.1
(58) Field of Search ............... 800/205, DIG. 52, 800/295, 298, 278; 435/172.3, 69.1, 320.1, 252.3, 419, 468, 292.3; 536/23.2, 23.6, 24.1

(56) References Cited

U.S. PATENT DOCUMENTS 5,126,324   6/1992  Clark et al. .
5,633,442 * 5/1997  Schell et al. ...................... 800/205

FOREIGN PATENT DOCUMENTS 0298918   1/1989  (EP) .
0375091   6/1990  (EP) .
9012097  10/1990  (WO) .

OTHER PUBLICATIONS

Watson et al. Rocombinant DNA, 1992, pp. 454–455.*
Thornburg et al. Proc. Natl. Acad. Sci. USA, 84: 744–748, 1987.*
Sanchez–Serrano et al. The EMBO Journal. 6(2), 303–306, 1987.*
Asano et al. Carlberg Res. Commun. 51, 129–141, 1986.*
Leah et al. Plant Molecular Biology. 12:673–682, 1989.*
Asano et al. (1986) *Carlsberg Res. Commun.* 51:129.
Darvill et al. (1984) *Ann. Rev. Plant Physiol.* 35:243.
Ebert et al. (1990) *Bioconjugate Chemistry* 1:331.
Goeddel et al. (1979) *Nature* 281:544.
Hahlbrock et al. (1979) Ann. *Rev. Plant Physiol.* 30:105.
Jun (1990) *Chemical Abstracts* 113:127723.
Leah et al. (1989) *Plant Mol. Biol.* 12:673.
Leah et al. (1991) *J. Biol. Chem.* 266:1564.
Potrykus (1991) *Annu. Rev. Plant Physiol. Plant Mol. Biol.* 42:205.
Roberts et al. (1986) *Biochim. Biophys. Acta* 880:161.
Sanchez–Serrano et al. (1987) *EMBO Journal* 6:303.
Stirpe et al. (1983) *Biochem. J.* 216:617.
Svendsen et al. (1982) *Carlsberg Res. Commun.* 47:45.
Thornburg et al. (1987) *Proc. Natl. Acad. Sci. USA* 84:744.
Watson et al. (1992) *Recombinant DNA* pp. 454–455.
Asano et al. (1984) Carlsberg Res. Commun. 49:619.
Chaudhry et al. (1994) The Plant Journal 8:815.

* cited by examiner

*Primary Examiner*—Lynette R. F. Smith
*Assistant Examiner*—Thomas Haas
(74) *Attorney, Agent, or Firm*—Baker Botts, LLP

(57) ABSTRACT

Described are a method of producing pathogen-resistant plants in which a protein-synthesis inhibitor gene or a fusion product of the protein-synthesis inhibitor gene or of the protein-synthesis inhibitor protein with ligands permitting specific attachment to cells is introduced into the genotype of plants under the control of an active promotor, and the use of the protein-synthesis inhibitor protein obtained by introducing the protein-synthesis inhibitor gene into the bacterial overproducers for making pharmaceutical preparations.

17 Claims, 12 Drawing Sheets

```
CTTAATAGCACATCTTGTCCGTCTCTTAGCTTTGCATTACATCCATGGCGGCAAAGATGGCG       60
                                       *          M  A  A  K  M  A
                                                 -1  1

AAGAACGTGGACAAGCCGCTCTTCACCGCGACGTTCAACGTTCCAGGCCAGTCCGCCGAC       120
 K  N  V  D  K  P  L  F  T  A  T  F  N  V  Q  A  S  S  A  D
               10                      20

TACGCCACCTTCATCGCCGGCATCCGCAACAAGCTCCGCAACCCGGCGCACTTCTCCCAC       180
 Y  A  T  F  I  A  G  I  R  N  K  L  R  N  P  A  H  F  S  H
               30                      40

AACCGCCCCGTGCTGCCCGGTCGAGCCCAACGTCCCGAGCAGGTGGTTCCACGTC       240
 N  R  P  V  L  P  P  V  E  P  N  V  P  P  S  R  W  F  H  V
               50                      60

GTGCTCAAGGCCTCCCCGACCAGCGCCGGCTCACGCTGGCCATTCGGCGACAACATC       300
 V  L  K  A  S  P  T  S  A  G  L  T  L  A  I  R  A  D  N  I
               70                      80

TACCTGGAGGGCTTCAAGAGCAGCGACGGCACCTGGTGGGAGCTCACCCCGGGCCTCATC       360
 Y  L  E  G  F  K  S  S  D  G  T  W  W  E  L  T  P  G  L  I
               90                     100

CCCGGCGCCACCTACGTCGGGTTCGGCGGGACCTACCGCGACCTCCTCGGCGACACCGAC       420
 P  G  A  T  Y  V  G  F  G  G  T  Y  R  D  L  L  G  D  T  D
              110                     120

AAGCTGACCAACGTCGCTCTCGGCCGCCAGCAGCTGGCGGACGCGGTGACCGCCCTCCAC       480
 K  L  T  N  V  A  L  G  R  Q  Q  L  A  D  A  V  T  A  L  H
              130                     140
```

FIG. 3A

```
GGGCGCACCAAGGCCGACAAGCCGTCCGGCCCCGAAGCAGCAGGAGGCGGTG      540
 G  R  T  K  A  D  K  P  S  G  P  K  Q  Q  Q  A  R  E  A  V
                    150                          160

ACGACGCTGCTCCTCATGGTGAACGAGGCCACGCGGTTCCAGACGGTGTCTGGGTTCGTG  600
 T  T  L  L  M  V  N  E  A  T  R  F  Q  T  V  S  G  F  V
            170                          180

GCCGGGTTGCTGCACCCCAAGGCGGTGGAGAAGAAGAGCGGGAAGATCGGCAATGAGATG  660
 A  G  L  L  H  P  K  A  V  E  K  K  S  G  K  I  G  N  E  M
        190                          200

AAGGCCCAGGTGAACGGGTGGCAGGACCTGTCCGCGGCTGCTGAAGACGGACGTGAAG    720
 K  A  Q  V  N  G  W  Q  D  L  S  A  A  L  L  K  T  D  V  K
    210                          220

CCTCCGCCCGGGAAGTCGCCAGCGAAGTTCGCGCCGATCGAGAAGATGGGCGTGAGGACG  780
 P  P  P  G  K  S  P  A  K  F  A  P  I  E  K  M  G  V  R  T
                230                          240

CTGTACAGGCCGCCAACACGCTGGGGATCCTGCTGTTCGTGGAGTGCCCGGGTGGGTTG   840
 A  V  Q  A  A  N  T  L  G  I  L  L  F  V  E  V  P  G  G  L
                    250                          260

ACGGTGGCCAAGGCGCTGGAGCTGTTCCATGCGAGTGGTGGGAAATAGGTAGTTTTCCAG  900
 T  V  A  K  A  L  E  L  F  H  A  S  G  G  K  *

GTATACCTGCATGGGTAGTGTAAAAGTCGAATAAACATGTCACAGAGTGACGGACTGATA  960

TAAATAAATAAACGTGTCACAGAGTTACATATAAACAAATAAATAATTAAAA          1020

ATGTCCAGTTTA₄₇                                                1078
```

FIG. 3B

```
GCGGTGACGACGCTGCTCCTCATGGTGAACGAGGCCACGCGGTTCCAGACGGTGTCGGGG     60
 A  V  T  T  L  L  M  V  N  E  A  T  R  F  Q  T  V  S  G
                     170                    180

TTCGTGGCCGGGCTGCTGCACCCCAAGGCGGTGGAGAAGAGCGGGAAGATCGGCAAT       120
 F  V  A  G  L  L  H  P  K  A  V  E  K  K  S  G  K  I  G  N
                     190                    200

GAGATGAAGGCCCAGTGAACGGGTGGCAGGACCTGTCCGCGCTGAAGACGGAC           180
 E  M  K  A  Q  V  N  G  W  Q  D  L  S  A  A  L  L  K  T  D
                     210                    220

GTGAAGCCCCCGCCGGGAAAGTCGCCAGCGAAGTTCACGCCGATCGAGAAGATGGGCGTG    240
 V  K  P  P  P  G  K  S  P  A  K  F  T  P  I  E  K  M  G  V
                     230                    240

AGGACTGCTGAGCAGGCTGCGGAGCAGGCGGCTACTTTGGGGATCCTGCTGTTCGTTGAGGTGCCGGGT  300
 R  T  A  E  Q  A  A  A  T  L  G  I  L  L  F  V  E  V  P  G
                     250                    260

GGGTTGACGGTGGCCAAGGCGCTGGAGCTGTTTCATGCGAGTGGTGGGAAATAGGTAGTT    360
 G  L  T  V  A  K  A  L  E  L  F  H  A  S  G  G  K  *
                     270                    280

TTGCAGGTATACCTGCATGGGTAAATGTAAAGTCGAATAAAAATGTCACAGAGTGACGG    420

ACTGATATATAAATTAATAAACATGTCATCATGAGTGACAGACTGATATAAATAAATA₂₀   499
```

FIG. 3C

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1032bp
      (B) TYPE: nucleic acid
      (C) STRANDEDNESS: double
      (D) TOPOLOGY: linear (ii) MOLECULE TYPE: cDNA (iii) HYPOTHETICAL: no (iv) ANTI-SENSE: no (vi) ORIGINAL SOURCE:
      (A) ORGANISM: Hordeum vulgare L. cv.
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(xi) SEQUENCE DESCRIPTION: SEQ ID NO: 1:

```
CTTAATAGCA CATCTTGTCC GTCTTAGCTT TGCATTACAT CC

ATG GCG GCA AAG ATG GCG                                                    60
Met Ala Ala Lys Met Ala
 -1   1           5

AAG AAC GTG GAC AAG CCG CTC TTC ACC GCG ACG TTC AAC GTC CAG GCC           108
Lys Asn Val Asp Lys Pro Leu Phe Thr Ala Thr Phe Asn Val Gln Ala
             10                  15                  20

AGC TCC GCC GAC TAC GCC ACC TTC ATC GCC GGC ATC CGC AAC AAG CTC           156
Ser Ser Ala Asp Tyr Ala Thr Phe Ile Ala Gly Ile Arg Asn Lys Leu
                 25                  30                  35

CGC AAC CCG GCG CAC TTC TCC CAC AAC CGC CCC GTG CTG CCG CCG GTC           204
Arg Asn Pro Ala His Phe Ser His Asn Arg Pro Val Leu Pro Pro Val
             40                  45                  50

GAG CCC AAC GTC CCG CCG AGC AGG TGG TTC CAC GTC GTG CTC AAG GCC           252
Glu Pro Asn Val Pro Pro Ser Arg Trp Phe His Val Val Leu Lys Ala
         55                  60                  65

TCG CCG ACC AGC GCC GGG CTC ACG CTG GCC ATT CGG GCG GAC AAC ATC           300
Ser Pro Thr Ser Ala Gly Leu Thr Leu Ala Ile Arg Ala Asp Asn Ile
 70                  75                  80                  85

TAC CTG GAG GGC TTC AAG AGC AGC GAC GGC ACC TGG TGG GAG CTC ACC           348
Tyr Leu Glu Gly Phe Lys Ser Ser Asp Gly Thr Trp Trp Glu Leu Thr
                 90                  95                 100

CCG GGC CTC ATC CCC GGC GCC ACC TAC GTC GGG TTC GGC GGC ACC TAC           396
Pro Gly Leu Ile Pro Gly Ala Thr Tyr Val Gly Phe Gly Gly Thr Tyr
             105                 110                 115
```

```
CGC GAC CTC CTC GGC GAC ACC GAC AAG CTG ACC AAC GTC GCT CTC GGC    444
Arg Asp Leu Leu Gly Asp Thr Asp Lys Leu Thr Asn Val Ala Leu Gly
        120                 125                 130

CGG CAG CAG CTG GCG GAC GCG GTG ACC GCC CTC CAC GGG CGC ACC AAG    492
Arg Gln Gln Leu Ala Asp Ala Val Thr Ala Leu His Gly Arg Thr Lys
    135                 140                 145

GCC GAC AAG CCG TCC GGC CCG AAG CAG CAG CAG GCG AGG GAG GCG GTG    540
Ala Asp Lys Pro Ser Gly Pro Lys Gln Gln Gln Ala Arg Glu Ala Val
150                 155                 160                 165

ACG ACG CTG CTC CTC ATG GTG AAC GAG GCC ACG CGG TTC CAG ACG GTG    588
Thr Thr Leu Leu Leu Met Val Asn Glu Ala Thr Arg Phe Gln Thr Val
            170                 175                 180

TCT GGG TTC GTG GCC GGG TTG CTG CAC CCC AAG GCG GTG GAG AAG AAG    636
Ser Gly Phe Val Ala Gly Leu Leu His Pro Lys Ala Val Glu Lys Lys
        185                 190                 195

AGC GGG AAG ATC GGC AAT GAG ATG AAG GCC CAG GTG AAC GGG TGG CAG    684
Ser Gly Lys Ile Gly Asn Glu Met Lys Ala Gln Val Asn Gly Trp Gln
    200                 205                 210

GAC CTG TCC GCG GCG CTG CTG AAG ACG GAC GTG AAG CCT CCG CCG GGA    732
Asp Leu Ser Ala Ala Leu Leu Lys Thr Asp Val Lys Pro Pro Pro Gly
215                 220                 225

AAG TCG CCA GCG AAG TTC GCG CCG ATC GAG AAG ATG GGC GTG AGG ACG    780
Lys Ser Pro Ala Lys Phe Ala Pro Ile Glu Lys Met Gly Val Arg Thr
230                 235                 240                 245

GCT GTA CAG GCC GCC AAC ACG CTG GGG ATC CTG CTG TTC GTG GAG GTG    828
Ala Val Gln Ala Ala Asn Thr Leu Gly Ile Leu Leu Phe Val Glu Val
            250                 255                 260

CCG GGT GGG TTG ACG GTG GCC AAG GCG CTG GAG CTG TTC CAT GCG AGT    876
Pro Gly Gly Leu Thr Val Ala Lys Ala Leu Glu Leu Phe His Ala Ser
        265                 270                 275

GGT GGG AAA TAGGTAGTTT TCCAGGTATA CCTGCATGGG TAGTGTAAAA GTCGAATAAA 935
Gly Gly Lys
        280

CATGTCACAG AGTGACGGAC TGATATAAAT AAATAAATAA ACGTGTCACA GAGTTACATA  995

TAAACAAATA AATAAATAAT TAAAAATGTC CAGTTTA                           1032

(2) INFORMATION FOR SEQ ID NO: 2:

(i) SEQUENCE CHARACTERISTICS:
        (A) LENGTH: 480bp
        (B) TYPE: nucleic acid
        (C) STRANDEDNESS: double
        (D) TOPOLOGY: linear (ii) MOLECULE TYPE: cDNA (iii) HYPOTHETICAL: no (iv) ANTI-SENSE: no (vi) ORIGINAL SOURCE:
        (A) ORGANISM: Hordeum vulgare L. cv.
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(xi) SEQUENCE DESCRIPTION: SEQ ID NO: 2:

GCG GTG ACG ACG CTG CTC CTC ATG GTG AAC GAG GCC ACG CGG TTC CAG     48
Ala Val Thr Thr Leu Leu Leu Met Val Asn Glu Ala Thr Arg Phe Gln
1               5                   10                  15
```

-continued

```
ACG GTG TCG GGG TTC GTG GCC GGG CTG CTG CAC CCC AAG GCG GTG GAG       96
Thr Val Ser Gly Phe Val Ala Gly Leu Leu His Pro Lys Ala Val Glu
            20                  25                  30

AAG AAG AGC GGG AAG ATC GGC AAT GAG ATG AAG GCC CAG GTG AAC GGG      144
Lys Lys Ser Gly Lys Ile Gly Asn Glu Met Lys Ala Gln Val Asn Gly
        35                  40                  45

TGG CAG GAC CTG TCC GCG GCG CTG CTG AAG ACG GAC GTG AAG CCC CCG      192
Trp Gln Asp Leu Ser Ala Ala Leu Leu Lys Thr Asp Val Lys Pro Pro
    50                  55                  60

CCG GGA AAG TCG CCA GCG AAG TTC ACG CCG ATC GAG AAG ATG GGC GTG      240
Pro Gly Lys Ser Pro Ala Lys Phe Thr Pro Ile Glu Lys Met Gly Val
 65                  70                  75                  80

AGG ACT GCT GAG CAG GCT GCG GCT ACT TTG GGG ATC CTG CTG TTC GTT      288
Arg Thr Ala Glu Gln Ala Ala Ala Thr Leu Gly Ile Leu Leu Phe Val
                85                  90                  95

GAG GTG CCG GGT GGG TTG ACG GTG GCC AAG GCG CTG GAG CTG TTT CAT      336
Glu Val Pro Gly Gly Leu Thr Val Ala Lys Ala Leu Glu Leu Phe His
            100                 105                 110

GCG AGT GGT GGG AAA TAGGTAGTTT TGCAGGTATA CCTGCATGGG TAAATGTAAA      391
Ala Ser Gly Gly Lys
        115

AGTCGAATAA AAATGTCACA GAGTGACGGA CTGATATAAA TAAATTAATA AACATGTCAT    451

CATGAGTGAC AGACTGATAT AAATAAATA                                      480
```

METHOD OF PRODUCING PATHOGEN-RESISTANT PLANTS

This is a continuation of application Ser. No. 08/375,186 filed on Jan. 18, 1995 now U.S. Pat. No. 5,633,442 which is a continuation of Ser. No. 07/810,390 filed Dec. 19, 1991, now abandoned.

The invention relates to a method of producing pathogen-resistant plants, plants and plant components produced by the method, new DNA transfer vectors and DNA expression vectors and finally the use of a protein-synthesis inhibitor protein for producing pharmaceutical preparations.

BACKGROUND OF THE INVENTION

It is known for example from Ann. Rev. Plant Physiol. 1979, 30: 105–130 and Ann. Rev. Plant. Physiol. 1984, 35:34–275 that plants utilize a great variety of mechanisms to protect themselves from infections by pathogens. These mechanisms include for example modifications in the cell wall structure, synthesis of toxically acting phytoalexines, accumulation of so-called PR proteins (pathogenesis-related proteins), protease inhibitors and enzymes with hydrolytic functions.

It is further known for example from Biochem. J. 1983, 216:617–625 that various plants can generate proteins which have the ability of inhibiting the ribosomes of eucaryotes. Characteristic of such proteins inhibiting protein synthesis is the property of not influencing the plant-inherent ribosomes whilst they inactivate the plant-foreign ribosomes. Such proteins have become known in particular under the designation "RIP" proteins (ribosome-inhibiting proteins). Of most of these proteins, only their molecular weight and their mode of action are known.

Among the plants in which RIP proteins have been found are the barleys. Thus, in Carlsberg Res. Commun. Vol. 51,1986, p. 129–141, the purified protein, the molecular weight thereof and the amino acid sequence are described.

It is further known, for example from Biochemica et Biophysica Acta 880, 1986, p. 161–170 that RIP proteins are able to inhibit "in vitro" pathogens.

SUMMARY OF THE INVENTION

In the investigation of in particular barley plants the genes which encode for protein-synthesis inhibitors (PSI) have been identified. It has been found that these PSI genes encode for PSI proteins which can effectively block the protein synthesis of plant pathogens.

It has further been found that PSI genes isolated for example from barley plants can be fused with a great variety of active promotors, for example the wun1-promotor, which is described in detail in "The Plant Cell 1", 1989, p.151–158 and that such promotor gene fusions can be incorporated into the genotype of plants and can produce transgenic plants which exhibit newly acquired pathogenic resistance.

It has further been found that the PSI protein can also be employed for producing pharmaceutical preparations which can be used to treat humans and animals affected by fungal, bacterial, viral or other pathogenic agents.

The PSI protein can be made in large amounts by introducing the PSI gene into bacterial overproducers. Purified PSI protein may be introduced in the form of infusion solutions into the blood path of humans or animals. The PSI protein inhibits the pathogen (for example AIDS viruses) without damaging the organism. The pathogen specificity of the PSI protein can possibly be further increased by coupling the PSI protein to pathogen-specific antibodies.

It is also possible to treat degenerate cells (cancer) in humans or animals by employing PSI protein. Thus, purified PSI protein or PSI protein which has been coupled to antibodies which detect specifically degenerate cells can be introduced into the blood path for destroying degenerate cells. Other forms of administration are possible, for example in capsules.

Suitable infusion solutions can be prepared by methods as usual and known for the preparation of aqueous infusion solutions.

Accordingly, the subject of the invention is a method of producing pathogen-resistant plants as is characterized in the claims, new DNA transfer vectors and DNA expression vectors as well as plants and plant components which can be obtained by the method according to the invention.

The subject of the invention is furthermore the use of the protein-synthesis inhibitor protein obtained by introduction of the protein-synthesis inhibitor gene into bacterial overproducers for the production of pharmaceutical preparations for the generation of pathogenic resistances, combatting pathogenic affection and/or degenerate cells.

Typical plant pathogens of which the protein synthesis can be inhibited by incorporation of a PSI gene are for example the fungi *Trichoderma reesei* and *Fusarium sporotrichioides*. (Attention is drawn to the review in M. Klinkowski, E. Mühle, E. Reinmuth and H. Bochow: "Phytopathology and plant protection I+II", Akademie-Verlag, Berlin, 1974).

As is known, fusarium fungi attack mainly cereals and maize plants whilst fungi of the genus Trichoderma are to be found mainly on maize kernels.

It has surprisingly been found that the pathogen-inhibiting properties of PSI genes isolated for example from barley plants can also be transferred to plants of different species. Thus, it has been found for example that under the control of an active promotor, for example the wun1-promotor, a PSI gene isolated from barley can be incorporated into the genotype of tobacco plants. Tobacco plants which thereupon produce the PSI protein exhibit newly acquired resistance properties against for example the plant pathogenic *Rhizoctonia solani*. Rhizoctonia causes the so-called root-killer disease (affection of stem and root) in various plants, including potato and tobacco plants. Thus, newly acquired resistance properties in plants are directly correlated to the expression of PSI genes.

Apart from barley, protein-synthesis inhibitor genes can be isolated for example from all monocotyl and dicotyl plants and fused with a great variety of active promoters, for example pathogen-inducible promoters, constitutive promoters, development-specific promotors, organ-specific promotors and inducible promoters.

The following can be named as examples of plants into the genotype of which the new protein-synthesis inhibitor genes can be incorporated under the control of an active promotor:

all monocotyl useful plants, such as cereals all dicotyl useful plants, such as solanaceae and cucurbitaceae.

The method according to the invention is thus particularly suitable for producing pathogen-resistant plants. However, through the expression of the protein-synthesis-inhibitor gene a resistance to insects, fungi, bacteria, viruses and viroids can also be achieved in humans and animals.

According to an advantageous further development, for executing the method according to the invention a protein-synthesis inhibitor gene is suitable which has the DNA sequence illustrated in FIG. 3A. However, it will be apparent to the person skilled in the art that apart from this DNA sequence similar DNA sequences can be used to solve the problem set, for example a DNA sequence according to FIG. 3B which in the 5' region has been completed by a corresponding cDNA clone.

The invention will be explained in detail hereinafter by way of example with reference to the isolation of a PSI gene from barley, fusion of said gene with an active promotor and transfer of the fusion product into the genotype of tobacco plants.

BRIEF DESCRIPTION OF THE DRAWINGS

The Figures serve for a more detailed explanation of the invention. They show in detail.

The SDS-gel-electrophoretic separation is shown of protein fractions which have been formed in the purification of CHI protein (row 2–5), PSI protein (row 7–11) and BGL protein (row 13–17) from barley seeds. With the aid of specific antibodies the corresponding proteins can be detected. The abbreviations mean:

% $(NH_4)_2SO_4$: Proteins which have been precipitated by the salt.

% sup.: Proteins which have not been precipitated by the salt.

CM: Proteins which have not been bound by the CM column.

fra.: Protein fraction from CM column.

pur.: highly pure protein.

MW: Protein-size standard in kDalton.

FIG. 2 Fungus growth test with purified protein

Spores of *Trichoderma reesei* (A) and *Fusarium sporotrichioides* (B) were grown in a total volume of 135 µl medium/well of a microtiter plate and mixed with 0.05–1.5 µg of the particular protein indicated. Each point marking is the result of 5 independent measurements with relative standard deviations of 3.6% for (A) and 7.3% for (B). 100% fungus growth leads to an $O.D._{540}$ of 0.40 (A) and 0.41 (B).

FIG. 3 Nucleotide sequence of the isolated PSI-cDNA clones

A: The cDNA clone is 1078 nucleotides large. It includes a 42 bp large 5'-untranslated region, an open read frame of 843 bp (the stop codon is marked with *) and a 193 bp large 3'-untranslated end. Possible polyadenylation signals are underlined. The amino acid sequence resulting from the open read frame is indicated beneath the corresponding sequence.

B: Nucleotide sequence of an incomplete PSI-cDNA clone. Possible polyadenylation signals are underlined.

Figure 4:
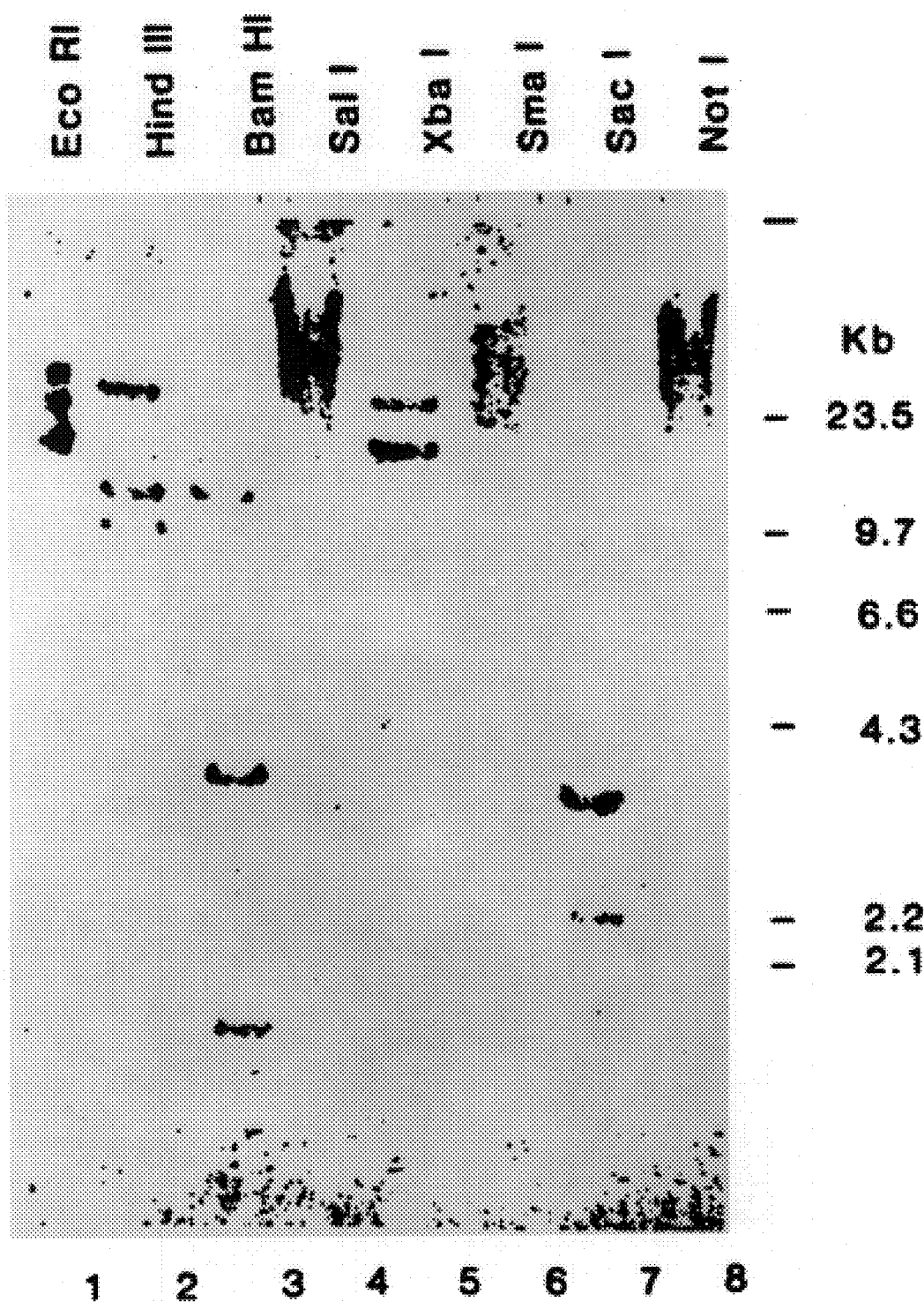

FIG. 4 Organization of PSI genes in the barley genome

DNA from barley embryos was cut with various restriction enzymes, gel-electrophoretically separated, transferred to nylon membranes and hybridized against radioactively marked PSI-cDNA. On the basis of the number of hybridizing bands conclusions can be drawn about the PSI copy number in the genome. The size standard is indicated in kilobase pairs (Kb).

Figure 5:
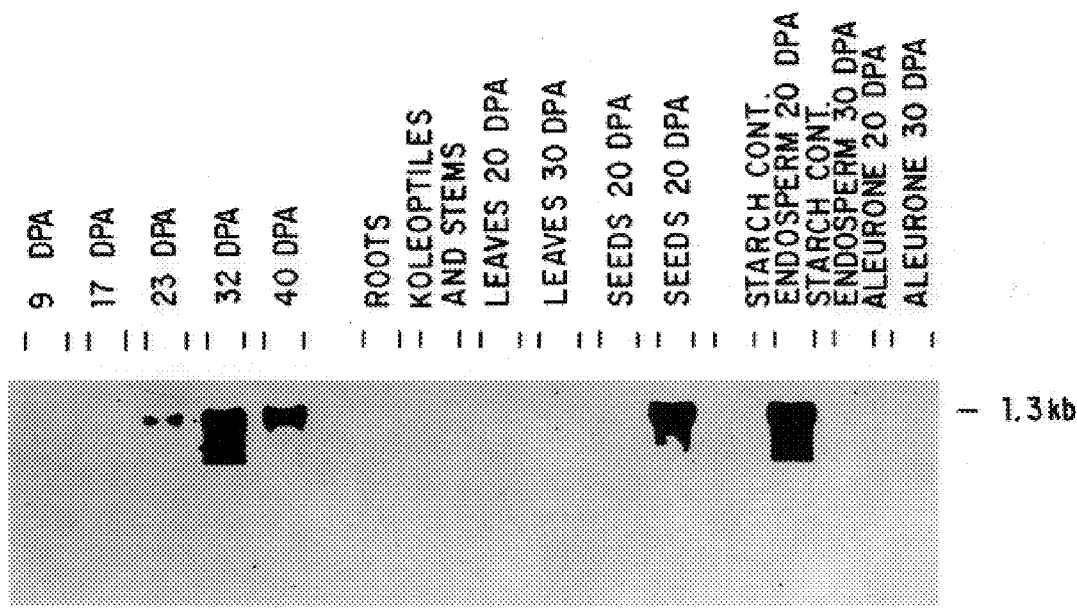

FIG. 5 Development-specific and organ-specific expression of PSI-RNA in barley

RNA was isolated from different organs of barley plants and at different development stages. The RNA was hybridized after gel-electrophoretic application via the "Northern Blot Method" with respect to radioactively marked PSI-cDNA. PSI-RNA is specifically detectable in the starch-containing endosperm during the subsequent seed development as 1.3 Kb large RNA. DPA stands for days after the anthesis.

Figure 6:
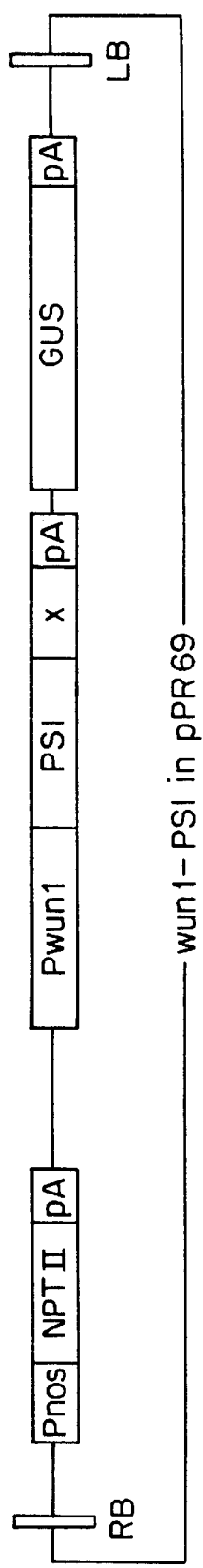

FIG. 6 Construction map of the chimeric gene wun1-PSI in pPR69

The wun1-promotor ("Pwun1"; about 1200 bp large) was fused transcriptionally with the PSI gene ("PSI"; about 1070 bp large). For RNA stability reasons, a residue of the CAT gene ("x"; about 500 bp large) and a polyadenylation signal ("pA"; about 200 bp large) were fused with the 3' of the PSI gene. This construct was cloned into the binary vector pPR69.

Figure 7:
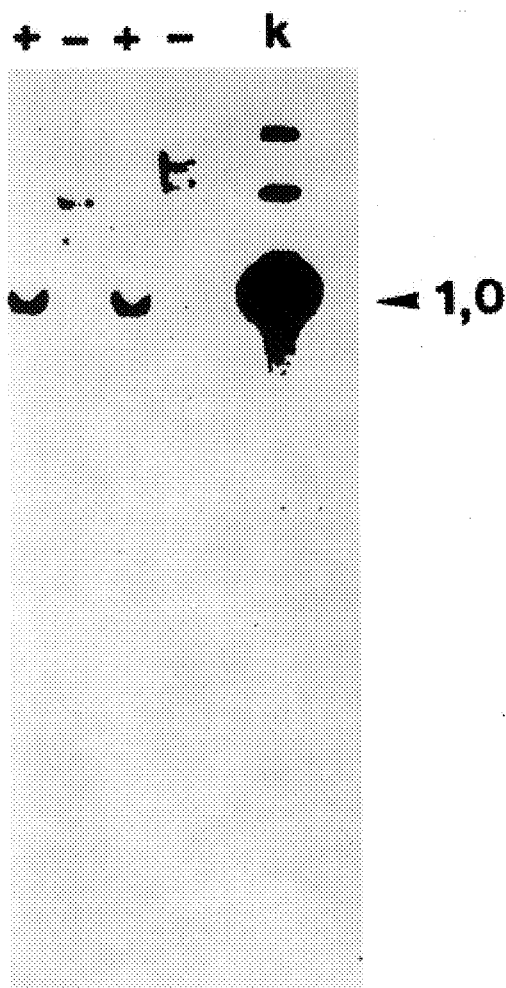

FIG. 7 Southern Blot Analysis of wun1-PSI-transgenic tobacco plants

To enable the correct integration of wun1-PSI-DNA into the tobacco genome to be analyzed, DNA was isolated from wun1-PSI-transgenic tobacco plants and cut with EcoRI. After the gel-electrophoretic separation of the DNA and the transfer of the DNA to nylon membranes hybridization was carried out with respect to radioactive PSI-cDNA. The plants designated with a (+) exhibit correct integration of the wun1-PSI-DNA. The size of the hybridizing bands is 1.07 Kb and is identical to the size of the plasmid-DNA of wun1-PSI in pPR69 (K) applied for control. Plants designated by (−) were discarded because of the presence of additional or incorrect large DNA bands.

Figure 8:
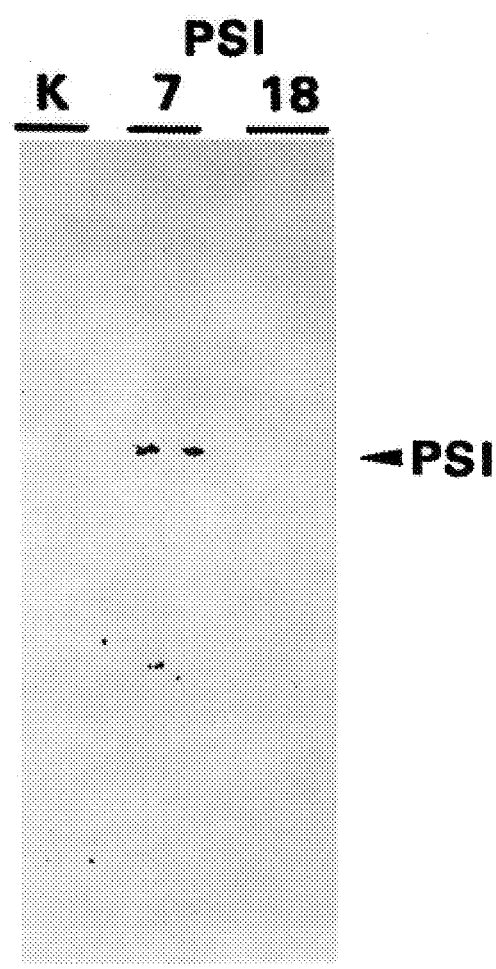

FIG. 8 Northern Blot Analysis of wun1-PSI-transgenic tobacco plants

100 µg leaf RNA from *Rhizoctonia solani* infected tobacco plants were separated gel-electrophoretically, transferred to nylon membranes and hybridized with respect to radioactive PSI-cDNA. On the autoradiography, in the case of wun1-PSI-transgenic tobacco plants ("PSI-7; PSI-18) a PSI-RNA band can be seen. In untransformed tobacco plants (K) no PSI-RNA can be detected.

Figure 9:
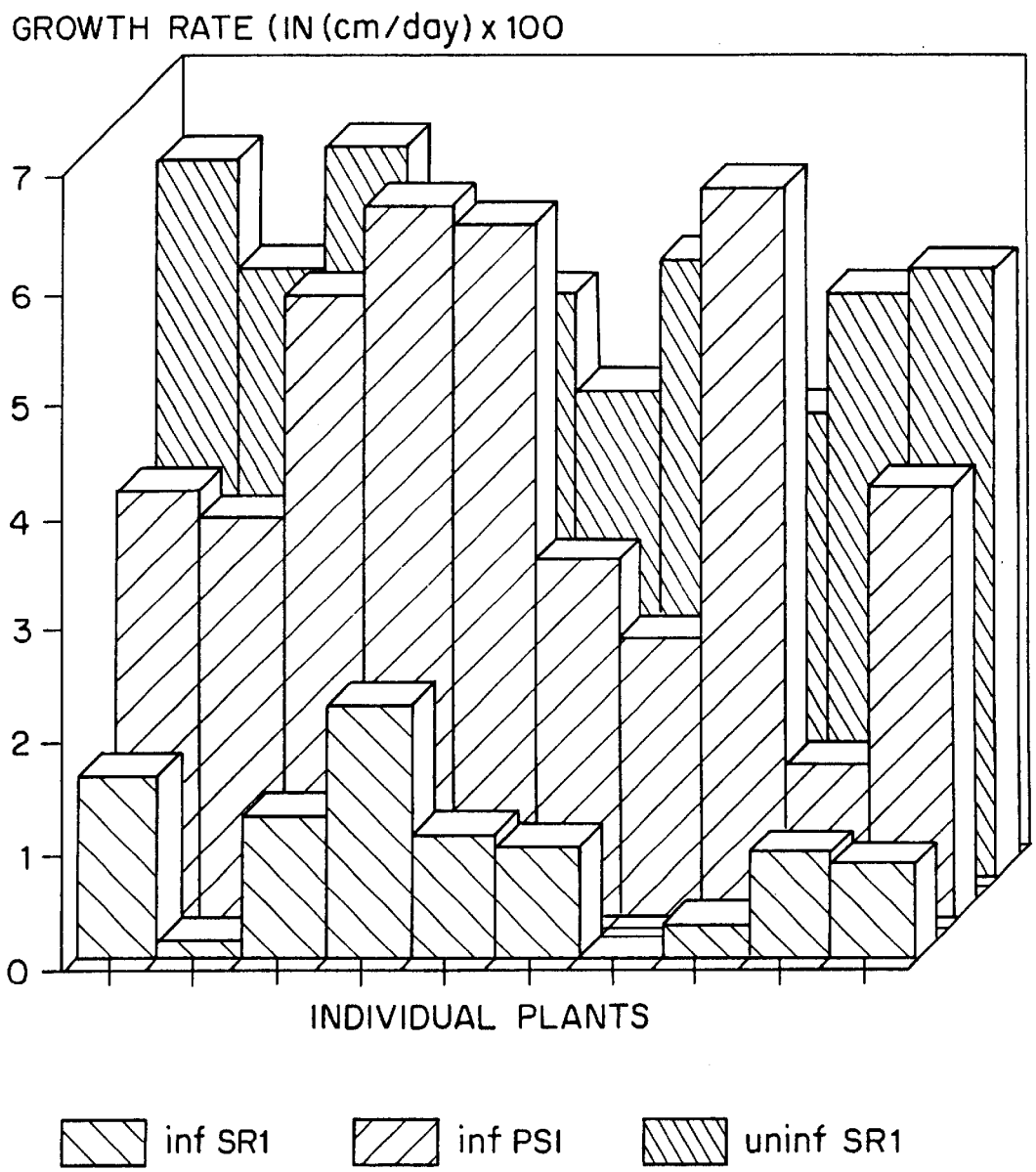

FIG. 9 Growth rates of individual tobacco plants infected with *Rhizoctonia solani*

Each bar illustrated represents the growth of a tobacco plant over a period of about 10 days. From the slope of the growth curve, the 1n×100 was calculated so that the value obtained represents the growth rate. "inf. SRI": untransformed tobacco which was infected with *Rhizoctonia solani*. "inf.RIP: wun1-PSI-transgenic tobacco which was infected with *Rhizoctonia solani*. "uninf.SRI: untransformed tobacco which was not infected.

Figure 10:
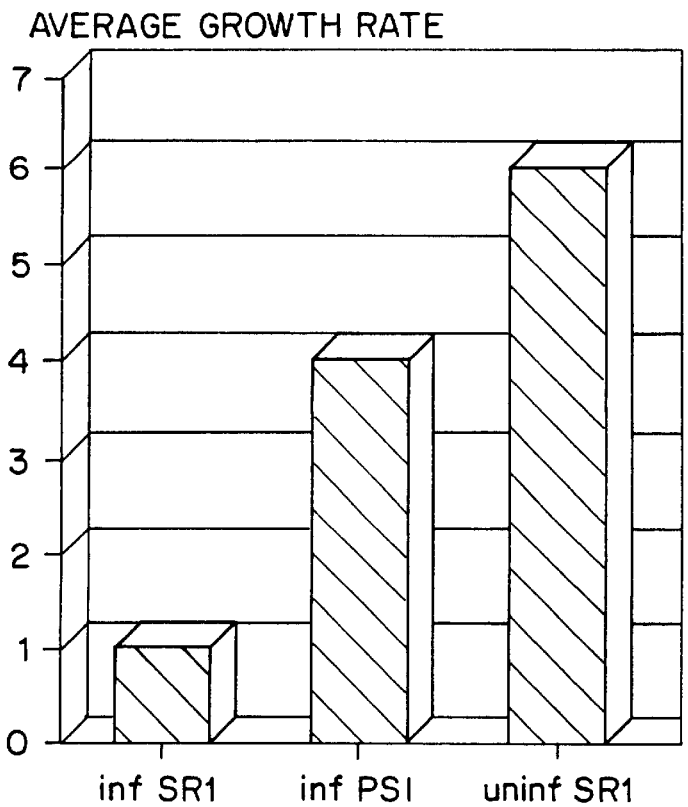

FIG. 10 Average growth rate with *Rhizoctonia solani*-infected tobacco plants

Illustration of the average growth rates which were calculated from the individual values shown in FIG. 9.

Figure 11:
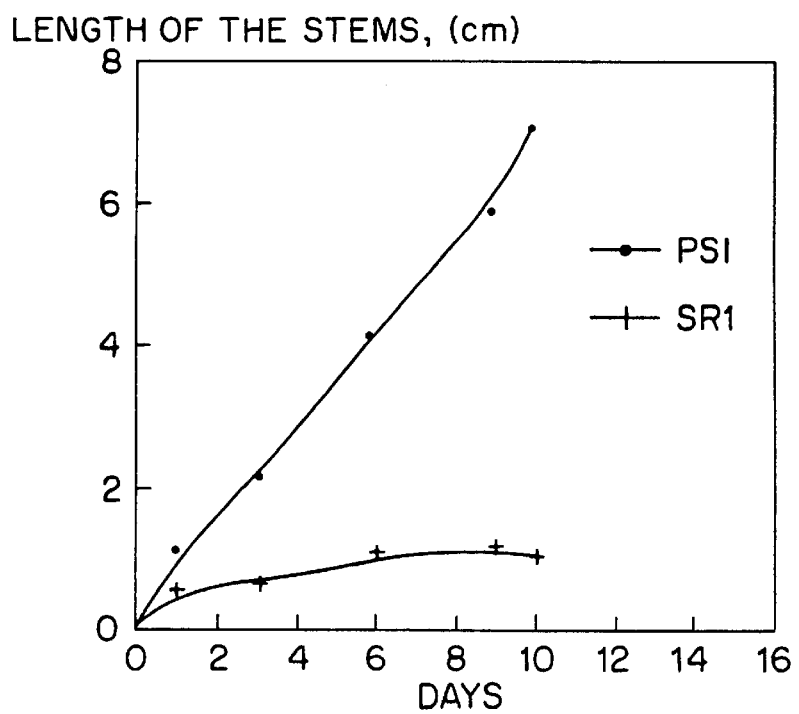

FIG. 11 Average stem growth of *Rhizoctonia solani*-infected tobacco plants

Average growth behaviour of 10 independent wun1-PSI-transgenic tobacco plants ("PSI") and 10 untransformed tobacco plants ("SRI") after infection with *Rhizoctonia solani*. Along the abscissa the length of the stem is plotted (up to the vegetation point) and along the ordinate the number of days after the infection.

EXAMPLE 1

A. Materials Used

Media

For cultivating bacteria, media were used as described in detail by Maniatis, T. et al in "Molecular cloning: a laboratory manual" Cold Spring Harbour Laboratory, Cold Spring Harbour, N.Y. (1982).

Plant Media

The media used are derived from the media (MS) specified by Murashige, T. et al in "A rapid method for rapid growth and bioassays with tobacco tissue cultures"; Physiol. Plant., 15:473–497 (1962).

3MS:MS+3% saccharose

3MSC:MS+3% saccharose, 500 µg/ml claforan

3MC15:MS+2% saccharose, 500 µg/ml claforan, +100 µg/ml kanamycin sulfate

MSC16:MS+0.5 µg/ml BAP+0.1 µg/ml NAA +100 µg/ml kanamycin sulfate +500 µg/ml claforan For solid medium, 8 g/l bacto agar were additionally added.

Strains and Vectors

E. coli strains:

BMH 71-18: delta(lac-proAB), thi, supE; F'(laci$^q$, ZdeltaM15, proA$^+$B$^+$)

Attention is drawn to: Messing, J. et al. "Plant Gene Structure" in: Kosuge, F., Meredith, C. P., Hollaender, A. (Eds.). Genetic engineering of plants. Plenum Press, New York: 211–227 (1983)

| | |
|---|---|
| Agrobacteria strains: | LBA 4404: (Hoekema et al., Nature 303: 179–180 (1983) |
| Plasmids: | pUC8 (Vieira and Messing in "The puc plasmid, an M13mp7-derived system for insertion mutagenesis and sequencing with synthetic universal primers. Gene, 19:259–268 (1982). |
| | pPR69 (a derivative of the bin 19, cf. "Bevan, M. Binary Agrobacterium vectors for plant transformation", Nucl. Acids, Res. 12: 8711–8721 (1984)). |
| Plants: | Hordeum vulgare L. cv. Piggy |
| | Nicotiana tabacum SRI |

B. Applied Methods

Unless otherwise indicated, all the molecular biological standard methods were carried out as in Maniatis et al., (1982), such as for example restriction analysis, plasmid isolation, minipreparations of plasmid-DNA, transformation of bacteria, etc.

Plant Material

Ripe barley seeds (Hordeum vulgare L. cv. Piggy) were harvested at various times after the anthesis, frozen in liquid nitrogen and stored at −80° C.

Isolation and Purification of PSI, CHI and BGL protein

PSI and CHI Protein 10 kg ripe barley seeds were worked to a fine flour (particle size: less than 0.5 mm in diameter). After addition of 100 liter extraction buffer (50 mM phosphate buffer, pH 6.5; 100 mM NaCl; 2.5 mM ascorbic acid; 2.5 mM EDTA; 3 mM beta-mercapto-EtOH) and stirring at 4° C. for 2 hours, the supernatant is filtered off. For this purpose, with the aid of an ultracentrifuge the volume of the supernatant is reduced to 6 liters (filters used: DDS membranes (ultrafiltration membranes of polysulphone) which retain all proteins smaller than 20 kDa). The supernatant is now precipitated with 40–70% $(NH_4)_2SO_4$. The pellet obtained is dissolved in 80 mM PMSF and dialyzed against 2 mM Na phosphate buffer, pH 6.5, to which 80 mM PMSF was added. The protein solution is now loaded via ion exchange chromatography on CM52 (Whatman) and eluted with 50 mM Na phosphate containing increasing NaCl concentrations (0.05 to 1.0 M NaCl with more than 10 elution steps).

BGL Protein

Barley seeds were germinated for 12 days, lyophilized and treated with extraction buffer (see above) (1.6 kg seed/25 liter extraction buffer). After a 40% $(NH_4)_2SO_4$ precipitation the supernatant was dialyzed and purified over a CM52 and mono-S column. Isolated BGL protein was tested as regards purity by western blots and N-terminal sequencing.

Preparation of PSI Antibodies

Antibodies were prepared with respect to purified PSI-II protein in rabbits by conventional methods Fungus Growth Test with Purified Protein Trichoderma reesei and Fusarium sporotrichioides (ATCC collection, Rockville) were grown on potato dextrose agar (Difco Co.) at 25° C. Spores of 8-day old cultures were harvested by the method of Broekaert, W. F. et al. "An automated quantitative assay for fungal growth inhibition" FEMS Microbiology Letters (1990) and stored at −20° C. in 20% glycerol. Within the scope of the fungus growth test a spore suspension (10000 spores/ml) was mixed with 100 µl potato dextrose solution and 35 µl of a protein fraction to be tested and incubated at 25° C. As described by Broekaert et al., the growth of the fungus is linearly correlated with the increase of the optical density at 540 nm. Protein fractions with fungus growth-inhibiting effect thus lead to a lower increase in the optical density than protein fractions with no effect.

Isolation of the PSI-cDNA Clones from Barley

From ripe barley seeds (Hordeum vulgare L cv. Piggy) polyA$^+$-RNA was isolated and deposited in a cDNA expression bank in lambda-gt-11 phages. Attention is drawn to Leah, R. and Mundy, J. "The biofunctional a-amylase/subtilisin inhibitor of barley; nucleotide sequence and patterns of seed-specific expression". Plant Mol. Biol. 12:673–682 (1989). With the aid of monospecific antibodies PSI (cf. Mundy, J. et al "Differential synthesis in vitro of barley aleurone and starchy endosperm proteins." Plant Physiol. 81:630–636 (1986) PSI-containing cDNA clones were identified.

Analysis of the PSI Nucleotide Sequence

PSI-positive lambda-gh11-phages were isolated, subcloned and sequenced by the didoxy sequencing method of Sanger et al., "DNA sequencing with chain-terminating inhibitors." Proc. Natl. Acad. Sci USA, 74:5463–5467 (1977).

DNA Transfer in Agrobacteria

Transformation

The DNA cloned in E. coli was transferred by the method described by Van Haute et al. in the work "Intergenic transfer and exchange recombination of restriction fragments cloned in pBR322: a novel strategy for reversed genetics of Ti-plasmids of Agrobacterium tumefaciens", EMBO J., 2:411–418 (1983), by conjugation to A. tumefaciens LBA4404 (cf. Hoekema et al. "A binary plant vector strategy based on separation of vir- and T-region of A-tumefaciens", Nature 303: 179–180 (1983)).

DNA Analysis

Checking of the DNA transfer to the agrobacterium was effected by isolation of the agrobacteria DNA by the method described by Ebert et al. in "Identification of an essential upstream element in the nopalin synthase promotor by stable and transient assays." Proc. Natl. Acad. Sci USA 84: 5745–5749 (1987). Restriction cleavage of the DNA, transfer to nitrocellulose and hybridization with respect to the corresponding radioactive probe providing information on a successful DNA transfer to agrobacterium.

Transformation of Tobacco Plants with Agrobacteria

Growth of Agrobacteria

The agrobacteria LBA4404 necessary for the infection were grown in selective antibiotica medium (cf. Zambrisky et al. "Ti-Plasmid vector for the introduction of DNA into plant cells without alteration of their normal capacity". EMBO J., 1:147–152 (1983)), sedimented by centrifugation and washed in YEB medium without antibiotics (YEB=0.5 meat extract; 0.2% yeast extract; 0.5% peptone; 0.5% saccharose; 2 mM $MgSO_4$). After again sedimenting and taking up in 3 MS medium, the bacteria could be used for the infection.

Leaf-Slice Infection

For the leaf slice infection sterile leaves of the tobacco lines SRI were employed. Leaf fragments of about 1 cm in size were dipped into the agrobacteria suspension described above and subsequently transferred to 3 MS medium. After incubation for 2 days with 16 hours light and at 25° C.–27° C., the leaf fragments were transferred to MSC16 medium. Shoots appearing after 4–6 weeks were cut off and placed on MSC15 medium. Shoots with root formation were further analyzed.

DNA Analysis of Plants

The plant material is pounded with liquid nitrogen, mixed with 10 volumes extraction buffer (10 mM tris-HCl (pH 8); 100 mM NaCl, 1 mM EDTA, proteinase K; pancreatic Rnase) and incubated, extracted with phenol and the supernatant precipitated with EtOH. The restriction digestion of the isolated DNA, the gel-electrophoretic separation of the DNA with Agarose and the transfer of the DNA to a nylon membrane is described in Maniatis et al. (1982). The hybridizing with respect to radioactively marked DNA specimens was carried out by a method described by Logemann et al. in the work "Improved method for the isolation of RNA from plant tissues", Anal. Biochem., 163:16–20 (1987).

RNA Analysis of Plants

Barley Plants

The isolation of total RNA and polyA$^+$RNA was carried out in accordance with Leah and Mundy et al. (1989). The gel-electrophoretic separation with formaldehyde gels, the transfer to nylon membranes and the hybridizing with respect to radioactively marked DNA specimens was carried out according to Maniatis et al. (1982).

Transgenic Tobacco and Potato Plants

The isolation of total RNA from various organs, the transfer to nylon membranes and the hybridizing with respect to radioactively marked DNA specimens was carried out according to Logemann et al. (1987).

Protein Analysis of Transgenic Plants

Lyophilized leaf material was pounded in the extraction buffer (10 mM tris pH 8.0; 1 mM EDTA; 100 mM NaCl; 2% SDS) and the protein concentration adjusted to 1 mg/ml. The gel-electrophoretic separation of the protein was carried out with the Phast-gel-system (Pharmacia), 1 μg protein per slot being applied. The separated proteins were transferred to nitrocellulose (diffusion blots by 20-minute application of the nitrocellulose to the protein gel at 70° C.) and analyzing by employing specific antibodies (western blot analysis according to the protoblot system of the Promega company).

Infection of Transgenic Plants with *Rhizoctonia solani*

The fungus *Rhizoctonia solani* is grown in a liquid medium (potato dextrose agar of the Difco company) at 28° C. and harvested after 5–6 days. By means of a Buchner funnel and connected suction bottle the medium is extracted. The remaining fungus mycel is cut into fragments as small as possible with a scalpel. The desired amount of fungus mycel is weighed in and thoroughly mixed with 5 liters of sterile standard soil. This soil was spread in a dish and the plants to be tested planted therein. The growth of the plants is determined every 24 hours by determining the shoot length (ground-vegetation point distance).

Results

Figure 1:
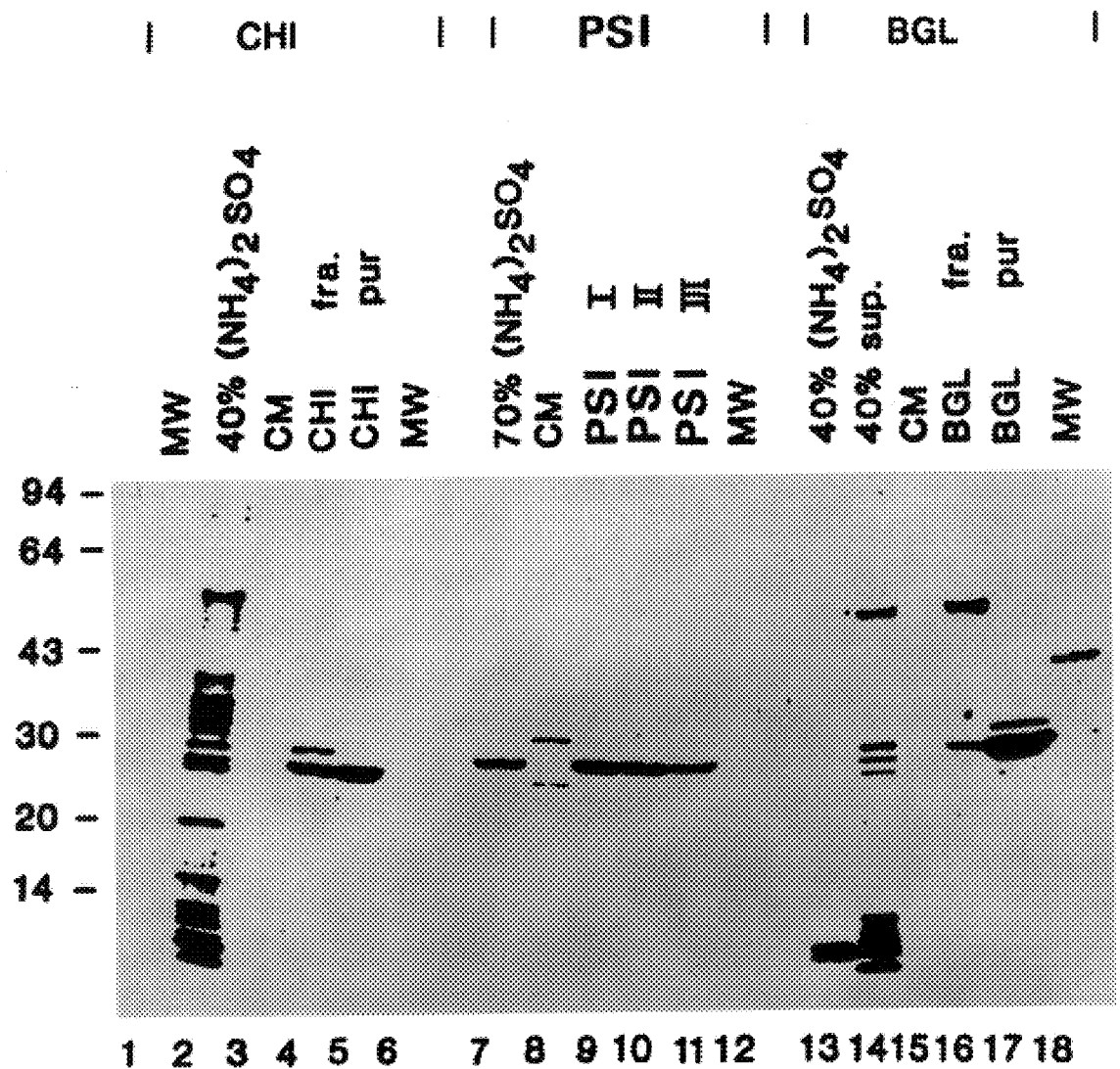
FIG. 1 Purification of CHI, BGL and PSI proteins from barley

Isolation and purification of PSI, CHI and BGL proteins from barley seeds:

The isolation of CHI and PSI protein from ripe barley seeds (*Hordeum vulgare* L. cv. Piggy) is described in "Methods". The protein fractions forming within the scope of the various purifying steps were applied to a denaturating acrylic amide gel and CHI or PSI proteins represented by silver-marked CHI or PSI antibodies (FIG. 1). CHI or PSI protein can be detected after 40% and 70% $(NH_4)_2SO_4$ precipitation (row 2, 7) after subsequent separation via Whatman CM52 (row 3, 4, 8) and after the following purification via a mono-S-column (row 5,9,10,11). Rows 9, 10 and 11 of FIG. 1 show that three different PSI isoforms (PSI I, II, III) have been isolated which distinguish themselves by their different running behaviour in the CM52 column.

The specific activity of purified CHI protein was determined in accordance with Molano et al., "A rapid and sensitive assay for chitinase using tritiated chitin", Anal. Biochem. 88:648–656 (1977) and is 22 mg diacetyl chitobiose/minute/mg protein.

The purified PSI protein exhibits the following activity:
3–30 ng PSI are able to inhibit 50% of the RNA translation in reticulocyte lysates.

BGL protein was purified from 12-day old barley seedlings by $(NH_4)_2SO_4$ precipitation, separation via CM52 and a mono-S column (see "Methods") and detected with the aid of BGL antibodies (FIG. 1, rows 13–17). The specific activity of purified BGL protein is 25 mg glucose-equivalent/minute/mg enzyme.

Fungus growth test with purified proteins

As described in "Methods", various geni of fungus are grown each on 135 μl fungus medium in microtiter plates (96 wells/plate) and their growth followed photometrically. By adding various proteins the influence of the latter on the fungus growth can be analyzed.

Figure 2A:
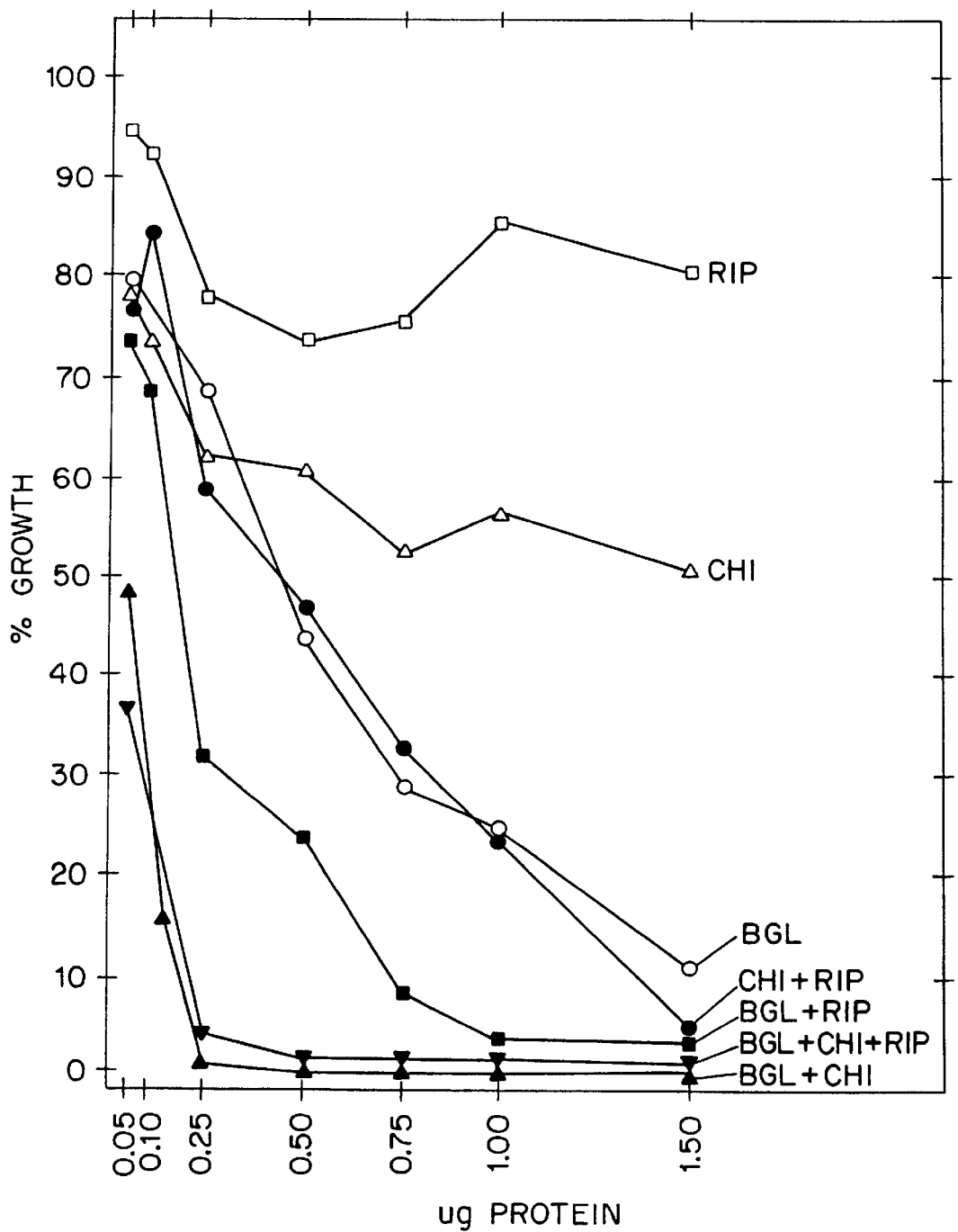

In FIG. 2A the growth behaviour of the fungus *Trichoderma reesei* is illustrated. The use of 1.5 μg PSI/well inhibits the fungus growth by only 20%. In contrast, the growth is inhibited by more than 95% if 0.25 μg of each of the proteins PSI, CHI and BGL are combined with each other. A 95% inhibition is also obtained by the combination PSI/BGL (in each case 1.0 μg protein) or by the combination PSI/CHI (in each case 1.5 μg protein).

Figure 2B:
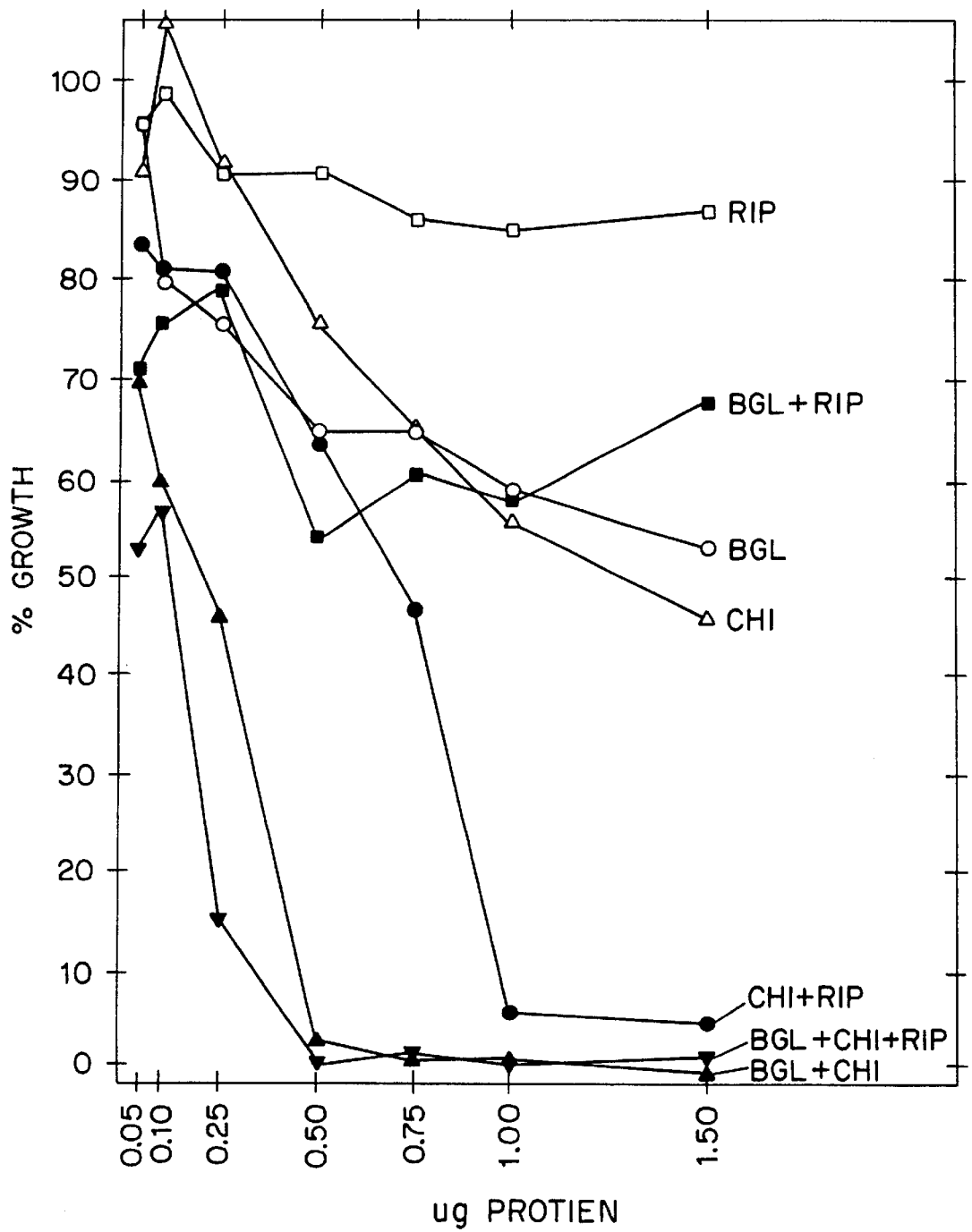

The growth of *Fusarium sporotrichioides* is also inhibited to 95% if 0.25 μg protein of each of PSI, CHI and BGL is combined (FIG. 2B). The combination PSI/CHI (in each case 1.0 μg protein) inhibits the fungus to the same extent. The use of 1.5 μg PSI or CHI or BGL alone however leads to significantly lower inhibitions. A lower effect is also obtained with the combination PSI/BGL.

The data determined in FIGS. 2A and 2B show that the use of PSI alone has a relatively low inhibition effect against the fungi used here. The combination with the chitinase CHI (FIGS. 2A, B) or with the glucanase BGL (FIG. 2A) however considerably enhances the inhibition effect.

Isolation and sequencing of a PSI-cDNA clone:

From ripe barley seeds of the type *Hordeum vulgare* L. cv. Piggy polyA$^+$RNA was isolated, transformed to cDNA and cloned in lambda-gt-11 phages (see "Material and Methods"). An almost complete PSI-cDNA clone could be identified by using PSI antibodies. Sequencing of the PSI-cDNA clone gave the following data (FIG. 3A):

The PSI clone has a length of 1087 bp.

The GC-rich open read frame encodes for a protein with a molecular weight of 29,976 Dalton.

The PSI protein does not contain any signal peptide.

The PSI protein starts with the amino acid methionine and thus conforms with the protein start of the naturally occurring PSI protein. It is therefore to be expected that the PSI protein is a cytosolic protein.

The DNA sequence shown in FIG. 3B is incomplete but does exhibit substantial homologies to the cDNA clone according to FIG. 3A and is suitable for solving the problem set if the DNA sequence shown in the 5' region is completed by a corresponding cDNA clone.

Detection of PSI genes in the barley genome:

The use of the PSI-cDNA clone as radioactive probe permits an analysis of the barley genome with regard to the organization and number of PSI genes. DNA was isolated from barley embryos, cut with various restriction enzymes and hybridized with respect to the PSI-cDNA specimen. As shown in FIG. 4, principally three fragments hybridize with respect to PSI; therefore, three PSI genes per haploid genome are to be expected.

Detection of PSI-mRNA in barley seeds:

The expression of PSI-mRNA in various organs of barley seeds and within the scope of the seed development was determined with the aid of northern blot analyses (see "Material and Methods"). As FIG. 5 shows, no PSI-mRNA is present in barley roots, stems and leaves or in the aleurone layer of barley seeds. In contrast, large amounts of PSI-mRNA are found in the starch-containing endosperm from seeds provided that the seeds are in a late development stage. No PSI-mRNA is present in young endosperm.

Fusion of a PSI gene with the wun1 promotor and transfer to tobacco plants:

As described in FIG. 6, the PSI-cDNA clone is transcriptionally fused with the wund and pathogen-inducible promotor wun1.

The wun1-promoter (1022 bp) and 179 bp of the 5'-untranslated region of wun1 is fused with the PSI-cDNA clone isolated via EcoRI from the cDNA bank. The PSI gene has its own polyadenylation signal, the functionality of which in dicotyl plants can however so far only be presumed. Two additional elements were cloned behind the PSI gene to increase the stability of the PSI-mRNA. An approximately 500 bp long subsequence of the CAT gene (CAT-chloro-amphenicolacetyl transferase) was fused at 3' of the PSI gene. At 3' of the CAT subsequence the polyadenylation signal of the 35S gene of the cauliflower mosaic virus was used as terminating signal, the functionality of which in dicotyl plants is known.

The chimeric gene wun1-PSI was cloned via the HindIII cutting points into the binary vector pPR69, the designation of which is now "wun1-PSI in pPR69". Wun1-PSI in pPR69 was transformed by means of the agrobacterium tumefaciens transformation system in tobacco plants and kanamycin-resistant tobacco plants regenerated.

Detection of the wun1-PSI gene in transgenic plants:

With the aid of the southern blot analysis the wun1-PSI transgenic tobacco plants were investigated with regard to the correct integration of wun1-PSI into the tobacco genome. As FIG. 7 shows, the size of the hybridizing DNA bands from the transgenic tobacco plants corresponds to the size of the fragment introduced. Correct integration of wun1-PSI into the tobacco genome is therefore probable.

Determinations of PSI gene expressions in transgenic tobacco plants:

50 μg total RNA was isolated from fungal infected wun1-PSI transgenic tobacco leaves and investigated for the presence of PSI-mRNA (FIG. 8). No PSI-mRNA was detected in untransformed tobacco plants, irrespective of whether the leaves were in tact, injured or fungally infected. In tobacco leaves of fungally infected transgenic plants an RNA band hybridizing with PSI is apparent. The detection of PSI proteins in transgenic tobacco plants was carried out by the western blot method.

Infection of wun1-PSI-transgenic tobacco plants with *Rhizoctonia solani*:

Various independent wun1-PSI-transgenic plants were placed as approximately 10 cm sized plants in soil which had been infected with *Rhizoctonia solani* (5 g/5 liters soil). By daily measuring the plant size (plant vegetation point—soil distance) the growth of the plants was recorded for the next approximately two weeks. The control plants used were untransformed tobacco plants which 1. were likewise planted in soil infected with *Rhizoctonia solani* (5 g/5 liters soil);

2. were planted in soil without addition of *Rhizoctonia solani*.

FIG. 9 shows the growth behaviour of the individual plants under the corresponding conditions. The growth rate of untransformed tobacco plants is very low in *Rhizoctonia solani*-containing soil. In contrast, Wun1-PSI-transgenic tobacco plants exhibit a substantially higher growth rate on soil containing *Rhizoctonia solani*.

The growth rate is only slightly less than the rate of (untransformed tobacco plants which had been grown in fungus-free soil.

FIG. 10 describes the statistical mean value from the individual values shown in FIG. 9.

FIG. 11 shows the average growth of tobacco plants under various conditions. In a period of about 10 days untransformed tobacco plants grow about 1 cm on *Rhizoctonia solani*-containing soil. Wun1-PSI-transgenic tobacco plants grow about 4 cm/10 days on *Rhizoctonia solani*-containing soil. Untransformed tobacco plants kept on *Rhizoctonia solani*-free soil grow about 6 cm in about 10 days.

EXAMPLE 2

Isolation and Purification of the PSI Protein from Bacterial Overproducers

An example of a suitable plasmid for bacterial overproduction of PSI proteins is the plasmid pKK223-3 (Manufacturer: Pharmazia).

An IPTG (isopropyl-β-D-thiogalactoside) inducible tac-promotor permits for example the production of PSI protein. Various restriction points immediately behind the tac-promotor permit transcriptional fusion of the PSI gene with the tac-promotor. A strong ribosomal terminator (rrn) effects a defined stoppage of the transcription.

The PSI ene was cloned via the EcoRI cutting point in 5'3'-orientation into the EcoRI cutting point of pKK233-3 and transformed to JM105 bacteria. These bacteria were grown in 100 ml LB medium (50 mg/ml ampecilline) at 37° C. with vigorous shaking up to an $O.D._{550}=0.4$ and thereafter mixed with IPTG (2.5 mM final concentration). A further incubation for 4 hours at 37° C. followed. Thereafter, the 100 ml bacteria culture was centrifuged off for 15 minutes at 2500 rpm (Christ centrifuge, 4° C.) and the bacteria pellet taken up in 50 mM tris pH 8.0. The suspension was sonified with ultrasonic sound (several times for 2 minutes with 60% pulses) until the viscosity dropped appreciably.

Analogously to the description in "Methods" for "isolation and purifying of PSI protein" the PSI protein was then precipitated with 40–70% $(NH_4)_2SO_4$ and purified by ion exchange chromatography, for example CM52.

The purified and sterile-filtered protein was suitable for preparation of infusion solutions for therapeutical uses in humans and animals.

What is claimed is:

1. An isolated DNA encoding a protein having the amino acid sequence of SEQ ID NO: 1.

2. The isolated DNA of claim 1 having the nucleotide sequence of nucleotides number 46 through 885 of SEQ ID NO: 1.

3. An isolated DNA having the nucleotide sequence of SEQ ID NO: 1.

4. An isolated DNA encoding a barley protein synthesis inhibitor wherein said DNA comprises nucleotides number 1 through 351 of SEQ ID NO: 2.

5. An isolated DNA encoding a barley protein synthesis inhibitor comprising the amino acid sequence of SEQ ID NO: 2.

6. A chimeric construct comprising the DNA of any one of claims 1–5 operably fused to a promoter active in plants.

7. The chimeric construct of claim 6 wherein said promoter is selected from the group consisting of a pathogen-inducible promoter, a constitutive promoter, a development-specific promoter, an organ-specific promoter, an inducible promoter and the wun1 promoter.

8. A DNA expression vector comprising the chimeric construct of claim 7.

9. A method of making a transgenic plant comprising transforming a plant or plant cell with the chimeric construct of claim 6.

10. A transgenic plant, or the transgenic progeny thereof, produced by the method of claim 9.

11. A transgenic plant, or a plant part therefrom, comprising the chimeric construct of claim 6.

12. An agricultural preparation comprising a protein synthesis inhibitor having the amino acid sequence of SEQ ID NO: 1.

13. An isolated protein having the amino acid sequence of SEQ ID NO: 1.

14. A method for inhibiting growth of a plant pathogenic fungus comprising applying a protein synthesis inhibitor having the amino acid sequence of SEQ ID NO: 1 to said fungus.

15. The method of claim 14, wherein said fungus is *Trichoderma reesei, Fusarium sporotrichioides* or *Rhizoctonia solani.*

16. The method of claim 14 wherein said protein synthesis inhibitor is applied in combination with one or more of a chitinase and a glucanase.

17. A DNA expression vector comprising a chimeric construct comprising the DNA of any one of claims 1–5 operably fused to a promoter active in plants.

* * * * *